United States Patent [19]

Schwab et al.

[11] Patent Number: 5,268,510
[45] Date of Patent: Dec. 7, 1993

[54] PROCESS FOR PURIFICATION OF ALKOXYLATED ALCOHOLS

[75] Inventors: Peter A. Schwab; Tonyette S. Sandoval, both of Austin, Tex.

[73] Assignee: Vista Chemical Company, Houston, Tex.

[21] Appl. No.: 958,561

[22] Filed: Oct. 8, 1992

[51] Int. Cl.$^5$ .............................. C07C 41/34
[52] U.S. Cl. .................. 568/621; 568/699; 568/616; 568/608
[58] Field of Search ............ 568/621, 699, 616

[56] References Cited

U.S. PATENT DOCUMENTS

| | | | |
|---|---|---|---|
| 3,245,884 | 4/1966 | Kraut | 568/621 |
| 3,847,754 | 11/1974 | Oliver | 568/621 |
| 4,143,072 | 3/1979 | Hetzel et al. | 568/621 |
| 4,306,943 | 12/1981 | Mori et al. | 568/621 |
| 4,745,230 | 5/1988 | Otten et al. | 568/621 |
| 5,012,013 | 4/1991 | Wimmer et al. | 568/621 |

FOREIGN PATENT DOCUMENTS 127303 7/1985 Japan ......................... 568/621

*Primary Examiner*—Howard T. Mars
*Attorney, Agent, or Firm*—Browning, Bushman, Anderson & Brookhart

[57] ABSTRACT

A process for reducing volatile, odor-causing impurities in alkoxylated alcohols comprising adjusting the pH of an alkoxylated alcohol product mixture containing such impurities to a range of from about 7 to about 8.5 to produce an alkaline alkoxylated alcohol mixture and steam stripping the alkaline alkoxylated alcohol mixture at an elevated temperature for a period of time sufficient to produce a steam stripped alkoxylated alcohol containing a reduced amount of odor-causing impurities.

7 Claims, No Drawings

PROCESS FOR PURIFICATION OF ALKOXYLATED ALCOHOLS

FIELD OF THE INVENTION

The present invention relates to the purification of alkoxylated alcohols and, more particularly, to the removal of volatile, odor-causing bodies from alkoxylated alcohols.

BACKGROUND OF THE INVENTION

Alkoxylated alcohols, commonly referred to as alkoxylates, find widespread use as surfactants in industrial and household cleaners, detergents and the like. These alkoxylated alcohols are produced by a number of different processes well known to those skilled in the art. Regardless of, and depending on, the process employed to produce the alkoxylated alcohols, various impurities are formed. For example, it is known that unreacted alcohols, polyethylene glycols, dioxane and various other reaction products formed during the alkoxylation reaction are present in the product mixture. These and other impurities cause or can lead to undesirable odors in the product mixture, a particularly troublesome problem when the alkoxylated alcohol is used in household cleaning compositions, e.g., liquid detergents, hard surface cleaners, etc.

It is known, in an attempt to remove impurities including the volatile, odor-causing bodies, to strip the alkoxylated alcohol product mixture with inert gases such as nitrogen or subject it to vacuum stripping. However, these processes do not remove enough of the volatile, odor-causing bodies to render the alkoxylated alcohol "low odor."

SUMMARY OF THE INVENTION

It is therefore an object of the present invention to provide an improved process for purifying alkoxylated alcohols.

Another object of the present invention is to provide a process for reducing the concentration of odor-inducing components in alkoxylated alcohols.

Yet a further object of the present invention is to provide a process for removing impurities including odor-causing bodies from ethoxylated alcohols.

The above and other objects of the present invention will become apparent from the description given herein and the appended claims.

In accordance with the above objects, an alkoxylated alcohol mixture containing unreacted alcohol, alkylene oxide and other impurities, e.g., unwanted reaction by-products, some of which are odor-causing, is adjusted to have a pH of from about 7 to about 8.5. The thus produced alkaline alkoxylated alcohol mixture is steam stripped at an elevated temperature to produce a steam stripped, alkoxylated alcohol with a reduced content of impurities, e.g., odor-causing bodies.

DESCRIPTION OF THE PREFERRED EMBODIMENT

The alkoxylated alcohols to which the present invention pertains are generically the alkylene oxide adducts of alcohols, particularly fatty alcohols. The alkoxylated alcohols can be represented by the general formula

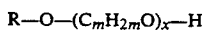

$$R-O-(C_mH_{2m}O)_x-H$$

wherein R is an organic radical containing from 1 to 30 carbon atoms, m is 2 to 4 and x is from 1 to 50. In the preferred case, the alkoxylated alcohols are those wherein R is a hydrocarbon radical, preferably a linear alkyl group preferably containing from about 6 to about 18 carbon atoms. Likewise, in the preferred case, m is 2, i.e., the alkylene oxide employed is ethylene oxide, and x is preferably from about 1 to about 12, particularly when m is 2.

Although, as noted above, the R group is preferably a hydrocarbon group, especially a linear or branched chained alkyl group, R can also be alkenyl, alkynl, aryl, alkyaryl or alicyclic in nature. R can also contain hetero atoms such as oxygen, sulfur, nitrogen, etc. For example, R can contain ether linkages, ketonic linkages, various sulfur-containing groups, etc. It is only necessary that R be free of groups containing active hydrogen atoms that would readily alkoxylate. Preferably, R will be a branched or straight chain hydrocarbon radical, i.e., an alkyl group, straight chain or linear hydrocarbon radicals being particularly preferred, particularly when the alkoxylated alcohols are used in surfactant applications.

The alkoxylated alcohols that can be purified according to the process of the present invention can be produced by methods well known to those skilled in the art. Generally, the alkoxylation processes that produce the alkoxylated alcohols are characterized by a condensation reaction, in the presence of a catalyst, of at least one epoxide with at least one organic compound containing at least one active hydroxyl hydrogen. Perhaps the most common catalyst, as disclosed in U.S. Pat. No. 4,223,164, is potassium hydroxide. Other patents disclosing processes for producing alkoxylated alcohols include U.S. Pat. Nos. 4,098,818; 4,210,764; 4,223,164; 4,239,917; 4,254,287; 4,302,613; 4,306,093; 4,453,022; 4,453,023; 4,820,673; and 4,835,321. As disclosed in the latter two patents, some of the alkoxylated alcohols are characterized by a narrow distribution of the alkoxylated species, such alkoxylated alcohols being commonly referred to as "peaked." The process of the present invention is applicable to the purification of any alkoxylated alcohol, whether of the peaked variety or of a type in which the alkoxylated species has a broader distribution such as is produced using a catalyst such as potassium hydroxide.

Depending upon the process employed to produce the alkoxylated alcohol, the pH of the product comprising the alkoxylated alcohol mixture can vary widely although typically it has a pH of from about 6 to about 10. For example, when a process such as disclosed in U.S. Pat. Nos. 4,820,673 and 4,835,321 is employed, the alkoxylated alcohol product mixture will generally have a pH of about 6. On the other hand, when alkali metal hydroxides are used as the catalyst, it is common for the product to have a pH of about 9 to 10. According to the process of the present invention, the pH of the alkoxylated alcohol mixture to be treated is adjusted to be in a range of from about 7 to about 8.5, preferably from about 7 to about 8. It will be understood that it is possible that the natural pH of alkoxylated alcohol mixtures from certain processes will inherently fall into the desired range of about 7 to 8, and, accordingly, the necessary adjustment to obtain the desired pH range will have been done in the process of producing the alkoxylated alcohol mixture. In other cases, however, it may be necessary to lower the pH by the use of acids such as acetic acid, phosphoric acid or the like. For example, in the case of alkoxylated alcohol mixtures produced using alkaline metal hydroxide catalysts, it is common to end up with a product mixture having a pH of about 9 or slightly greater. In such cases, the pH is adjusted to the desired range of 7 to 8.5, preferably 7 to 8, using a suitable acid that does not deleteriously affect the alkoxylated alcohol mixture. In cases, such as noted above, where the pH of the product mixture from the alkoxylation process has a pH of about 6, the pH can be adjusted upwardly to the desired range using sodium hydroxide, potassium hydroxide, etc.

It will be appreciated that the higher the pH during the steam stripping step, the greater the removal of odor-causing impurities. Thus at a pH of 9, greater odor reduction can be achieved than in the desired range of 7 to 8.5. However, at pH values greater than about 8.5, there is a dramatic increase in color-forming bodies.

Once the alkoxylated alcohol mixture has been adjusted to the desired pH range, it is steam stripped at an elevated temperature, care being taken to avoid excessively high temperatures that will cause side reactions or deleteriously affect the alkoxylated alcohol mixture. Steam stripping of the alkaline alkoxylated alcohol mixture can be conducted by the generation of steam in situ from water present in, or added to, the alkoxylated alcohol product mixture; or, external steam may be introduced into the alkaline alkoxylated alcohol mixture to effect the stripping.

It will be apparent to those skilled in the art that the temperature at which the steam stripping is conducted will depend upon the pressure used, the type of steam stripping employed and the composition of the product mixture. Alkoxylated alcohol product mixtures vary widely in composition and degree of impurities depending upon the starting materials used, type of alkoxylation process employed, etc. Accordingly, a wide range of temperatures, pressures and times of steam stripping can be employed. For example, in the case of in situ steam stripping, it is convenient to subject the alkaline alkoxylated alcohol mixture to sub-ambient pressure, the temperature being high enough to generate steam from the water present in the mixture at the given pressure. In the case where the steam stripping is conducted with the use of externally added steam, the alkoxylated alcohol mixture will generally be heated to a temperature sufficiently high enough to prevent excessive condensation of the externally added steam in the mixture. Accordingly, the steam stripping can be carried out over a wide range of temperatures and pressures depending upon whether in situ steam stripping is used or steam stripping is conducted by the use of externally added steam. In general, when in situ steam stripping is employed, temperatures will range from about 90° C. to about 120° C., pressures ranging from about 1 to about 20 mm. When external steam stripping is used, temperatures of from about 150° C. to about 190° C., preferably from about 170° C. to about 190° C., will be used, pressures ranging from about ambient to about 10 psig.

The amount of steam stripping, i.e., the time of steam stripping, will depend, as noted above, on the composition of the product mixture, the amount of impurities present in the product mixture, etc. Generally speaking, times ranging from about 10 minutes to about 3 hours are sufficient to reduce odor-causing impurities to a level that renders the steam stripped product acceptable as having "low odor." It will be appreciated, however, that longer times may be employed if necessary.

Although as noted above, in the past alkoxylated alcohol mixtures have been subjected to stripping with inert gases or vacuum stripping to remove volatile impurities, theses processes have not been successful in removing the volatile odor bodies to a low enough concentration to render the alkoxylated alcohol "low odor." Using the present process, it is possible to remove enough of the volatile odor-causing materials to render the alkoxylated alcohol "low odor" without inducing unwanted color in the product. Not only does the process of the present invention reduce the concentration of the odor-causing impurities to a level that renders the alkoxylated alcohol low odor, the process also results in the removal of other objectionable impurities such as dioxane, which has been deemed to be a health hazard. Accordingly, by using the process of the present invention, not only are the alkoxylated alcohols rendered low odor, but they are also rendered environmentally more acceptable.

To more fully illustrate the present invention, the following non-limiting examples are employed. In the examples that follow, the alkoxylated alcohols were all ethoxylated, i.e., they were ethylene oxide adducts of various alcohols. It will be understood, however, that the process of the present invention is equally applicable to the removal of odor-causing impurities from other alkoxylated alcohols such as propoxylated alcohols, ethoxylated-proproxylated alcohols, etc.

EXAMPLE 1

This example demonstrates in situ steam stripping. In this procedure, 250 g of NOVEL II 1012-62 ethoxylate (a $C_{10}$–$C_{12}$ alcohol ethoxylated with 62 percent by weight ethylene oxide and marketed by Vista Chemical Company) was employed. The general procedure was to introduce the ethoxylated alcohol together with 5 g of water into a one-liter single-neck round-bottom flask, which was then attached to a Buchi Rotovapor RE 120, which in turn was connected to a vacuum pump. The flask was rotated in a water bath at 100° C. for 30 minutes. The vacuum pump was then turned on and the pressure gradually decreased to a reduced pressure of 10 mm, which was maintained for 30 minutes. Following stripping, the ethoxylate was submitted to an odor panel for odor evaluation. The results are tabulated in Table 1 below. In the case of the odor panel evaluation, a higher number indicates a higher level of odor, whereas a lower number indicates "low odor."

TABLE 1

| Sample No. | Condition | Odor Panel Evaluation |
|---|---|---|
| 25-1 | Unstripped Starting Material pH 6.0 | 120 |
| 73-1 | Stripped pH 6.2 | 108 |
| 73-2 | Stripped pH 7.1[1] | 53 |
| 51-1 | Stripped pH 7.2[1] | 44 |
| 51-1A | pH 7.2 Aged 1 month[2] | 66 |

[1]Adjusted with NaOH from an initial pH of 6.
[2]Sample aged in a closed container at room temperature.

As can be seen from the data in Table 1, the unstripped, starting ethoxylate, i.e., the alkoxylated product mixture, which has a pH of 6, shows an unacceptably high odor. Even a stripped material (73-1) having a pH of less than 7, i.e., 6.2 shows a high odor level.

However, in cases where the pH is adjusted to be between 7 and 8 (Samples Nos. 73-2 and 51-1), steam stripping as per the process of the present invention greatly reduces the odor level and in fact, renders the products "low odor." The data in Table 1 also reveal that an ethoxylated alcohol that has been steam stripped according to the process of the present invention (51-1A) when subjected to aging shows an increase in odor level.

EXAMPLE 2

This example demonstrates the use of external steam to effect the stripping of the ethoxylated alcohol. In this case, the ethoxylated alcohol used was NOVEL II 1216-CO-60 (a mixture of $C_{12}$–$C_{14}$–$C_{16}$ alcohols ethoxylated with 60 percent by weight ethylene oxide marketed by Vista Chemical Company). The ethoxylated alcohol was placed in a 2 gallon stainless steel stirred autoclave and heated to 177° C. using sufficient high pressure (150 psi) steam injected into the bottom of the autoclave to raise the pressure to 4 psig on the outlet. Stripping was continued for 45 minutes followed by 30 minutes of nitrogen purging. pH adjustment was effected using sodium hydroxide. The stripped ethoxylate was submitted to odor panel evaluation and analysis for head space GC (HSGC) and water content. The results are shown in Table 2 below.

TABLE 2

| Sample No. | Conditions | % $H_2O$ | HSGC | Odor Panel Evaluation |
|---|---|---|---|---|
| 58-2 | Unstripped Starting Material pH 6.0 | 0.09 | 120 | 120 |
| 32-5 | pH 6.0 | 0.19 | 132 | 71 |
| 33-5 | pH 9.2 | 0.18 | 7 | 25 |

As can be seen from the data in Table 2, the unstripped, starting ethoxylate exhibits unacceptably high odor (see Sample No. 58-2). Steam stripping at a pH below 7, e.g. 6, also results in a stripped ethoxylate of unacceptably high odor level (see Sample No. 32-5). Steam stripping of the ethoxylate that has been adjusted to a pH of 9.2 (see Sample No. 33-5) results in a product that can be considered low odor. It should be further observed, as can be seen from the HSGC analysis, that a significantly greater amount of volatile impurities are removed from the ethoxylate when the stripping is conducted at high pH value. Compare, for example, the HSGC analysis of Sample Nos. 58-2 and 32-5 with Sample No. 33-5. However, there is an undesirable increase in color when the stripping is conducted at a pH greater than 8.5.

As noted with respect to the data in Table 1, although an alkoxylated alcohol of low odor can be achieved using the process of the present invention, storing or aging of the stripped alkoxylated alcohol results in an increase in odor level. It has been found that by adjusting and maintaining the pH of the stripped alkoxylated alcohol in the range of from about 6 to about 7, the subsequent formation of odor-causing impurities is prevented. Accordingly, the present invention also contemplates adjusting the pH of the steam stripped alkoxylated alcohol to a slightly acidic condition to prevent the formation of odor-causing bodies during storage.

EXAMPLE 3

This example shows the effects of controlling the pH of the alkoxylates steam stripped as per the process of the present invention in preventing the subsequent formation of odor-causing bodies. Three samples that had been steam stripped according to the process of the present invention were aged in an oven at 44° C. for 8 weeks and their odor compared with a corresponding sample that had been aged at room temperature. The odor panel then determined if there was a difference between the odors of the two samples. The results are shown in Table 3 below.

TABLE 3

| Sample No. | pH | Differences in Odor |
|---|---|---|
| 33-5 | 9 | Yes |
| 55-1 | 7.1–7.2 | Yes |
| 55-2 | 6.5[1] | No |

[1]Adjusted with phosphoric acid.

As can be seen from the data in Table 3, if the stripped alkoxylated alcohol is maintained at a pH greater than 7 following the steam stripping treatment according to the process of the present invention, there is an increase in odor-forming bodies (see Samples No. 33-5 and 55-1) as compared with a steam stripped alkoxylate that has been adjusted to a pH range of from 6 to 6.5 using phosphoric acid (see Sample No. 55-2).

It will be apparent that to prevent the formation of odor-forming bodies in stored or aged stripped alkoxylated alcohol, it is desirable to acidify the stripped alkoxylated alcohol with a substantially odor-free acid such as phosphoric acid so as to maintain the pH of the alkoxylated alcohol in a range of from about 6 to about 6.5.

The foregoing disclosure and description of the invention is illustrative and explanatory thereof, and various changes in the methods steps may be made within the scope of the appended claims without departing from the spirit of the invention.

What is claimed is:

1. A process for reducing volatile impurities in alkoxylated alcohols comprising adjusting the pH of an alkoxylated alcohol product mixture containing said impurities to an alkaline range up to a pH of about 8.5 to produce an alkaline alkoxylated alcohol mixture, steam stripping said alkaline alkoxylated alcohol mixture at an elevated temperature to produce a steam stripped alkoxylated alcohol containing a reduced amount of said impurities, and adjusting the pH of the steam stripped alkoxylated alcohol to an acidic range down to a pH of about 6.

2. The process of claim 1 wherein said alkoxylated alcohol has the general formula $$R-O-(C_mH_{2m}O)_x-H$$

wherein R is an organic radical containing from 1 to 30 carbon atoms, m is 2 to 4, and x is from 1 to 50.

3. The process of claim 2 wherein R is a hydrocarbon radical.

4. The process of claim 2 wherein m is 2.

5. The process of claim 2 wherein x is from about 1 to about 12.

6. The process of claim 3 wherein R contains from about 6 to about 18 carbon atoms.

7. The process of claim 6 wherein R is a straight chain alkyl group.

* * * * *